(12) United States Patent
Graves

(10) Patent No.: US 7,475,507 B2
(45) Date of Patent: Jan. 13, 2009

(54) SCENTED PICTURE FRAME

(75) Inventor: Peter Graves, Palos Park, IL (US)

(73) Assignee: Potomac Corporation, Wheeling, IL (US)

( * ) Notice: Subject to any disclaimer, the term of this patent is extended or adjusted under 35 U.S.C. 154(b) by 151 days.

(21) Appl. No.: 11/474,014

(22) Filed: Jun. 23, 2006

(65) Prior Publication Data

US 2008/0016743 A1 Jan. 24, 2008

(51) Int. Cl.
*A47G 1/06* (2006.01)
(52) U.S. Cl. .............................. 40/725; 40/755; 40/765; 40/768; 40/776
(58) Field of Classification Search .................. 40/700, 40/722, 725, 755, 757, 765, 768, 776; 239/54, 239/57; D23/366
See application file for complete search history.

(56) References Cited

U.S. PATENT DOCUMENTS

| 849,111 | A | * | 4/1907 | Fairchild | 40/786 |
|---|---|---|---|---|---|
| 2,172,273 | A | * | 9/1939 | Chilcote | 40/755 |
| 2,577,320 | A | * | 12/1951 | Fenyo | 239/55 |
| D269,902 | S | | 7/1983 | Edwards | |
| 4,814,212 | A | | 3/1989 | Spector | |
| 4,993,177 | A | * | 2/1991 | Hudson | 40/725 |
| 5,279,880 | A | | 1/1994 | Cohart | |
| 5,361,522 | A | * | 11/1994 | Green | 40/725 |
| D366,107 | S | | 1/1996 | Shaffer | |
| 5,950,922 | A | * | 9/1999 | Flinn | 239/34 |
| 6,052,933 | A | * | 4/2000 | Lytle | 40/711 |
| D435,100 | S | | 12/2000 | Pesu | |
| D439,964 | S | | 4/2001 | Wu | |
| D479,742 | S | | 9/2003 | Hollingworth | |
| 6,643,967 | B1 | * | 11/2003 | Bloom | 40/789 |
| 2003/0200690 | A1 | * | 10/2003 | Galloway | 40/779 |
| 2004/0057975 | A1 | * | 3/2004 | Maleeny et al. | 424/401 |

\* cited by examiner

*Primary Examiner*—Gary C Hoge
(74) *Attorney, Agent, or Firm*—James D. Palmatier

(57) ABSTRACT

The present invention is directed to a scented picture frame having removable scent boards attached in spaced relation to provide an aromatic ambiance with the display of an item such as a picture. The present invention features a holder on the back of the frame, capable of holding one or more scent boards in parallel adjacent the back of the frame, whereby an aroma is dissipated from a scented oil on the scent board to enhance the experience of viewing the item. Scents are impregnated into the scent board and retained by individually wrapping the scent boards for future use. One or more scents may be used with the present invention by hanging multiple scent boards on the scented picture frame. The scent boards may be removed and replaced when the scent is dissipated or to change the aroma. A picture pouch is used to protect the item in the scented picture frame from absorbing an aroma of the scent board.

19 Claims, 4 Drawing Sheets

SCENTED PICTURE FRAME

TECHNICAL FIELD

The present invention relates to a scented picture frame for use in a car, at home or in any room. The present invention is not funded by Federally Sponsored Research and does not relate back to any prior application.

RELATED PRIOR ART

Picture frames are well known in the art for providing device for displaying pictures, certificates and other mementoes. Picture frames are designed to hold one or more pictures in a viewable position to allow observation without touching the picture. In addition, scented cutouts are used to hold and disperse a scent into cars and rooms to deodorize and freshen the air and provide aromatic ambience by dispersing a scent into the air.

Prior art discloses a variety of devices for combining an air freshener with a photo frame. Design patent No. DES. 269,902 for COMBINED AIR FRESHENER AND PHOTO FRAME OR SIMILAR ARTICLE issued Jul. 26, 1983 discloses an air freshener chamber with a recessed pocket on one or both sides to hold a picture. It is unclear how the '902 patent dispenses a fragrance into the air.

Alternatively, an AUTOMOBILE AIR FRESHENER UNIT, U.S. Pat. No. 4,814,212 to Daniel Spector, discloses a picture holder for sticking on a car window. The picture frame has a porous frame impregnated with a volatile fragrance. The frame has a transparent window for holding and protecting a picture between the window and the car window and held in place with the frame. U.S. Pat. No. 5,361,522 for an AIR FRESHENER PICTURE FRAME, and a COMBINATION PICTURE FRAME AND AIR FRESHENER RECEPTACLE, U.S. Pat. No. DES 366,107 to Kevin Shaffer discloses a picture frame with an enclosure on the backside for retaining an air freshener material and a window on the front for displaying a picture.

The prior art does not disclose a convenient, inexpensive and compact picture frame having removable attachable fragrance sheets. The prior art also does not disclose a lightweight frame safe for use in a car or vehicle having alternate fragrance sheets attachable to the frame for covering odors, or creating an ambiance in the vicinity of the frame.

Smell is known to be a strong link to memory in human beings. The scent and fragrance technology allows manufacturers to synthetically create smells and aromas to create an atmosphere for mood setting. Aromatherapy has created oils and aromatic scents for keeping people alert, reducing stress, and other mood altering scenarios. In some cases different aromas are used together to create a desired effect.

In addition, the user of this device may want to change the smell or scent or aroma to correspond to a desired or present situation. The prior art does not disclose an easy to change scented picture frame for use in a car of home environment. The prior art discloses devices requiring liquid or other messy additions to add a scent or odor to a frame. Furthermore, the prior art does not provide an inexpensive, easy and clean way to change or remove the scent source.

The present invention solves this problem by integrating a frame having a tab on projecting from the back of the frame for removeably engaging one or more separate scent boards. The present invention is shipped as a kit having separate, individually wrapped scent boards for removable attachment to the frame. The separate scented board could be attached to or removed from the frame for changing the aroma in the surrounding area. The present invention is adapted to be hung in a car as an air freshener or mood enhancer or to be placed in a room such as in a home by standing the frame on a table or other surface having the scented board hidden from view. The scented board is replaceable with a similar scented board or a scented sheet having a different scent.

The present invention is designed to remedy this deficiency in the prior art by a frame having a separate, removable scented board. The frame may be placed in a viewing position by hanging from a support or in an alternate embodiment, standing the frame on a table or surface. The scent board is easily removed or replaced with out disassembly or destruction of the frame.

SUMMARY OF THE INVENTION

An object of the present invention is to provide a picture frame having a removable scent board fur use as a room deodorizer.

Another object of the present invention is to provide a picture frame having a scent board mounted outside the body of the frame to prevent scent impregnation into the frame for removal or changing scents.

Another object of the present invention is to provide a scented picture frame having removable, outboard scent boards.

Another object of the invention is to provide a picture frame having a tab on the frame wherein a plurality of scent boards may be removably attached to create an ambient aroma of mixed scents for aromatic enhancement of the surrounding air.

The present invention is directed to a scented picture frame having removable scent boards attached in spaced relation to provide an aromatic ambiance with the display of an item such as a picture. The present invention features a holder on the back of the frame, and out of sight of a viewer looking at the item, capable of holding one or more scent boards in parallel adjacent the back of the frame, whereby an aroma is dissipated from a scented oil on the scent board to enhance the experience of viewing the item. Scents are impregnated into the scent board and retained by individually wrapping the scent boards for future use. One or more scents may be used with the present invention by hanging multiple scent boards on the scented picture frame. The scent boards may be removed and replaced when the scent is dissipated or to change the aroma. A picture pouch is used to protect the item in the scented picture frame from absorbing an aroma of the scent board.

DETAILED DESCRIPTION OF THE INVENTION

Figure 1:
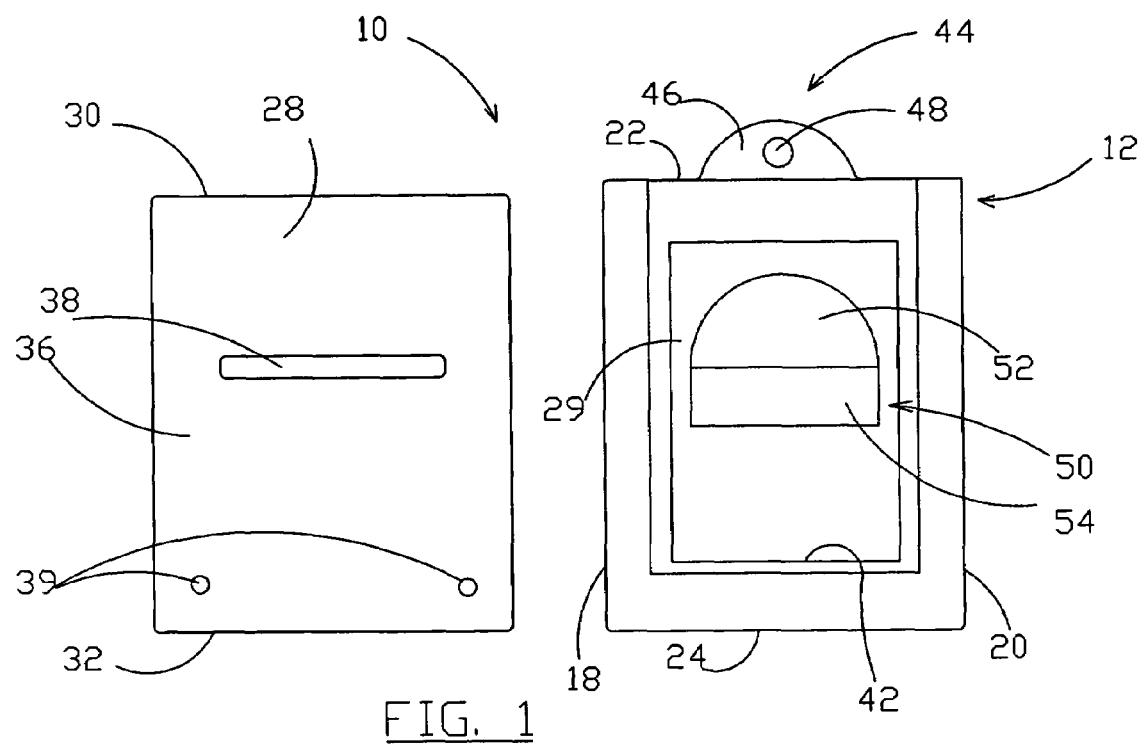
FIG. 1 is a front exploded elevation of the present invention showing the scent board separate from the frame body.

The present invention is illustrated in FIG. 1 shows an exploded view of the scented picture frame 10 having a body 12, the body comprising a front 14, a back 16 (FIGS. 2, 4), a first side 18, a second side 20, a top 22, and a bottom 24. A picture window 42 is formed in the front 14. A prop 44 may be a stub 46 having an aperture 48 formed therein. The frame 10 may be hung from a fixture in a viewable position. A scent sheet holder comprising a tab 50 is shown in outline on the back of the frame 10. The tab 50 has a loose end 52 and a base 54. The base 54 is attached to the back 16 of the frame. The loose end 52 extends upward toward the top 22 from the base 54. Tab 50 may be attached to the body 12 or may be die cut from the back-most layer 29 having the base 54 integral with the back 16.

Continuing to refer to FIG. 1, the scent board 28 comprises a scent impregnated sheet having a top 30, a bottom 32, an inside 34 (FIG. 2) and an outside 36. A slot 38 is formed through the scent board 28 from the inside 34 to the outside 36. The slot 38 is adapted to slidingly receive the loose end 52 of the tab 50 into the slot 38. The slot 38 may be any shape for adapting to the scent sheet holder on the back 16 of the body 12. Spacer knobs 39 may be formed on or attached to scent board 28. The knobs 39 allow multiple scent boards 28 to be positioned on a tab 50 by holding the scent boards 28 in spaced relation creating an air space 55 adjacent the scent board 28. The knobs 39 may also be used to identify the scented side of the scent board 28 for facing away from the back 16.

Figure 2:
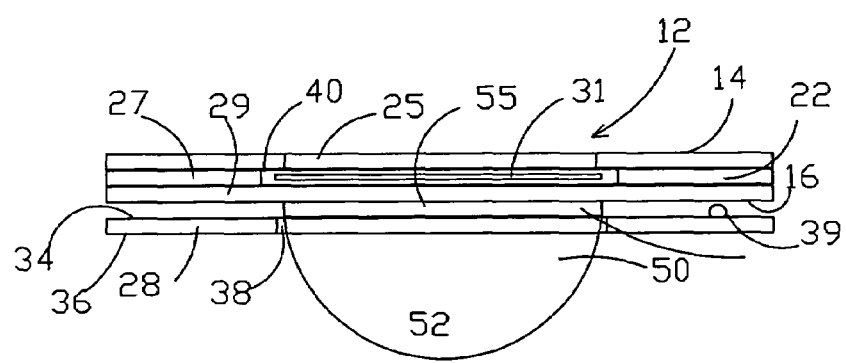
FIG. 2 is a bottom view of the present invention having the scent board mounted thereon.

Referring to FIG. 2, the frame 10 is shown as a laminated assembly having a face sheet 25 on the front 14, a spacer 27 behind the face sheet 25 and a support sheet 29 on the back 16. The top 22 has a picture slot 40 formed in the spacer 27 adjacent the top 22. The picture slot 40 is in communications with a picture cavity 53. The picture slot 42 and picture cavity 53 are formed by material removed from the spacer 27 in an area behind the picture window 42. A picture pouch 31 is shown in the picture slot 42 to hold and protect a picture (not shown) in the picture cavity 53. The picture pouch 31 is a preferably a square pocket of two flat, clear plastic sheets, sealed on three sides having a clear window adjacent the picture window 42 and an open side for inserting the picture (not shown). The picture pouch 31 protects the picture (not shown) from the aroma oils in the scent board 28. The frame 10 may be made of cardboard and the aroma oils or carrier on the scent board 28 may leach onto the support 29 and penetrate the body 10. To protect the picture (not shown) the picture is inserted through the fourth, open side of the picture pouch 31 and the pouch 31 is placed into the picture slot 42 with a viewable side facing the picture window 42 through the clear picture pouch 31.

Continuing to refer to FIG. 2, the frame 10 has tab 50 on the back 16. The tab 50 may be a separate piece attached by glue or other means to the support 29 at the back 16 or alternatively, die-cut from the support sheet 29. The tab 50 may extend at an angle to the back 16 to engage the scent board 28 and extend through slot 38 to hold scent board 28 in close proximity and approximately parallel relation to the back 16. The scent board 28 is removably attached to the body 12 by the loose end 52 extending through the slot 38. Gravity urges the scent board 28 to slide down along tab to a position between the loose end 52 and the base 54 and adjacent to the back 16. The knobs 39 hold the scent board 28 in spaced relation to create air space 55 for air circulation and scent dissipation.

Figure 3:
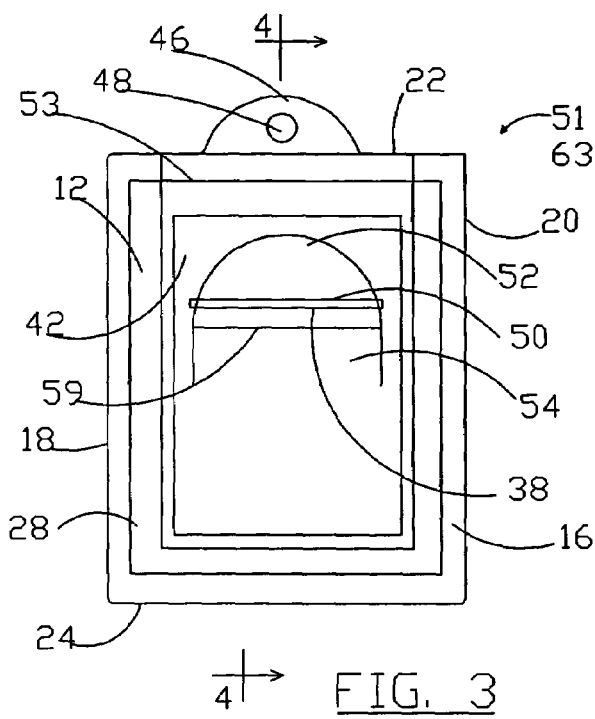
FIG. 3 is a rear elevation view of the present invention having the scent board separate from the frame.

Referring to FIG. 3, a rear view of the frame 10 illustrates the tab 50 die cut in support 29. In this embodiment, the base is integral with the back 16 and the tab 50 can be pushed out of the die cut 57 creating fold 59 to allow the tab to extend from the back 16 at an angle. The tab 50 is generally centered between the sides 18, 20. Prop 44 is centered to hold the frame 10 in a viewable position 51 having the picture window 42 vertically oriented. A fixture 61 such as a hook or automobile mirror may support the scented frame 10 by a string 63.

Figure 4:
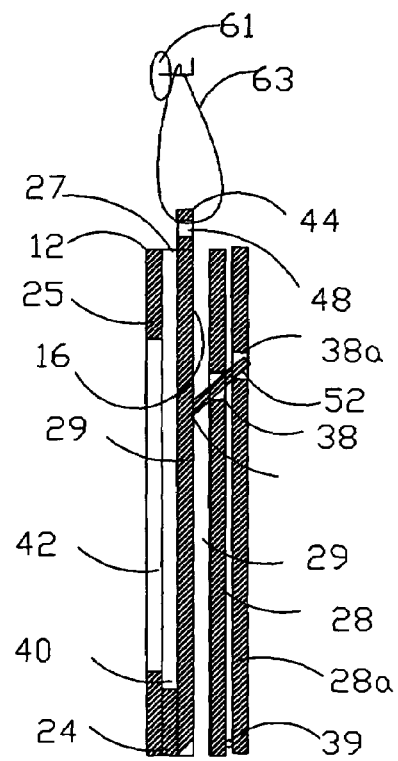
FIG. 4 is a side section view of the present invention taken at approximately 4-4 of FIG. 3.

Referring to FIG. 4, the laminated layers, face sheet 25, spacer 27 and support 29 are attached parallel to each other. The scent board 28 hangs on tab 50 extended through slot 38 having a first scent. The scent is applied using a carrying agent such as oil to hold the aroma on the scent board 28 and release the scent over a predetermined time period. The scented oil may leach to the body 12. Pouch 31 (FIG. 2) provides protection to the item in the picture window 42. Scent board 28 may be coated or impregnated with a first aroma agent on the out side 36 and an unscented on the inside 34. The second scent board 28a may have a second, different scent. Knobs 39 are positioned on the scent board 28, 28a to create an air space 55. The knobs 38 extend from the outside 36 or inside 34 to engage the back 16 or the second scent board 28a to create air space 55. Second scent board 28a is likewise slidingly mounted on tab 50 extended through slot 38a.

Figure 5:
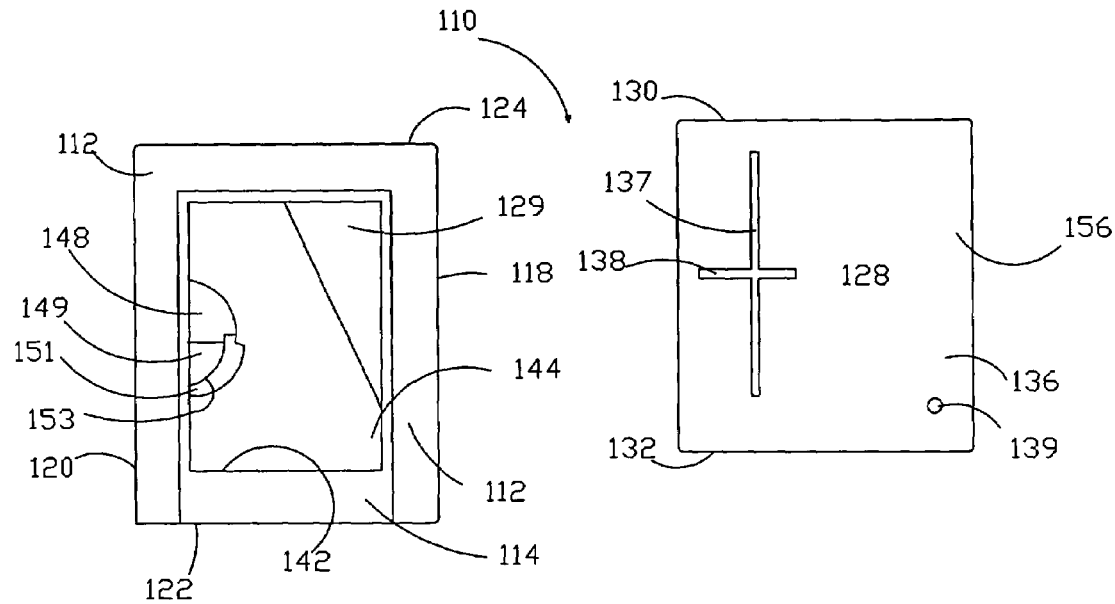
FIG. 5 is a front exploded elevation of the present invention in a second embodiment having the scent board separated from the frame.

Referring to FIG. 5, frame 110 is shown in an alternate embodiment. Frame 110 has a body 112, the body 112 comprising a front 114, a back 116 (FIG. 6), a first side 118, a second side 120, a top 122, and a bottom 124. A picture window 142 is formed in the front 114. A prop 144 is formed in the support sheet 129 as seen through the picture window 142. The prop 144 of the second embodiment is formed from cutouts in the support sheet 129. The prop 144 comprises a foot 147 and a lock 148. The lock 148 has a slide portion 149 for guiding the foot 147 into a standing position engaging the lock 148. Removing the cutout piece 151 exposes the edge 153 forming the slide portion 149. Foot 147 is engaged by lock 148 and held in position as is well known in the art of die cut, pop-out standing picture frames.

Continuing to refer to FIG. 5, the scent board 128 has a top 130 and a bottom 132. A dimple 139 is formed extending from the outside 156 to identify the scented side and space an adjacent scent board from the scent board 128. First slot 138 is formed generally horizontally in the scent board 128 to matingly receive the lock 149. Second slot 137 is formed in scent board 128 at an angle to first slot 138 and positioned to matingly receive the foot 147. Scent board 128 has a size and profile adapted to be eclipsed by the size and profile of frame 110 when the scent board 128 is mounted on frame 110 so the scent board 128 is generally not readily visible from the front 114.

Figure 6:
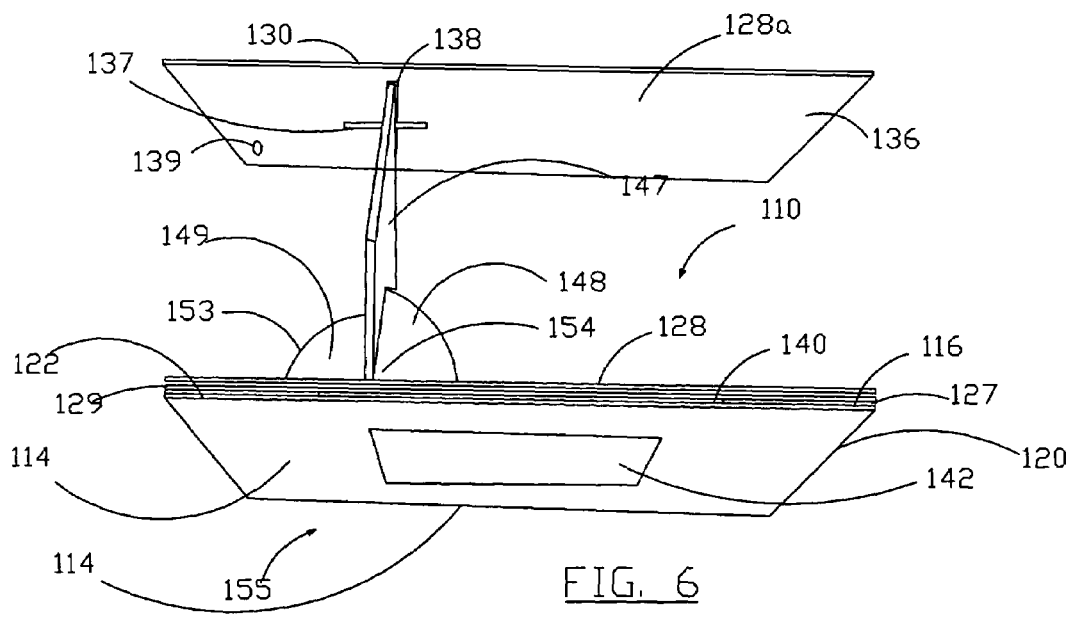
FIG. 6 is a top perspective view of a second embodiment of the present invention having the scent board mounted thereon.

Referring to FIG. 6, frame 110 is shown with the prop 144 comprising the foot 147 and lock 148 assembled in the stand up position 155. Foot 147 is integrally formed by a cut out of support sheet 129. Foot 147 further comprises a hinge side 154 on the frame 110. The lock 148 is bent to extend out from the back 116 for receiving the foot 147 as it is folded out from the back 116. The lock 148 and foot 147 engage to hold the foot extended from the back for supporting the frame 110 in a standing position 155. Lock 148 and foot 147 intersect and engage in the locked position at approximately a right angle. The foot 147 and lock 148 extending from the back 116 form the sheet holder. The scented board 128 has slots 137 and 138 adapted to slidingly receive the foot 147 and lock respectively to hold scent board 128 on frame 110. As should be understood, additional scent boards may be removably attached to frame 110 in a similar manner and held separated by knobs 139 (FIG. 6) on the outside 136.

Continuing to refer to FIG. 6, the scented picture frame 110 has a body 112 formed of laminated layers similar to the first embodiment of FIGS. 1-4. The picture slot 140 is in the top 122 intermediate the front 114 and the back 116. The picture slot 140 is adjacent to the picture window 142 in the front 114. The scented picture frame 110 stands on a table or surface having the bottom 124 resting thereon and the foot 147 supporting the frame 110 in a viewable position 155. The scented board 128 structurally supports the foot 147 and lock 149 engagement. A second scent board 128a may be hung on the tab to add an alternative aroma to the ambient air.

Figure 7:
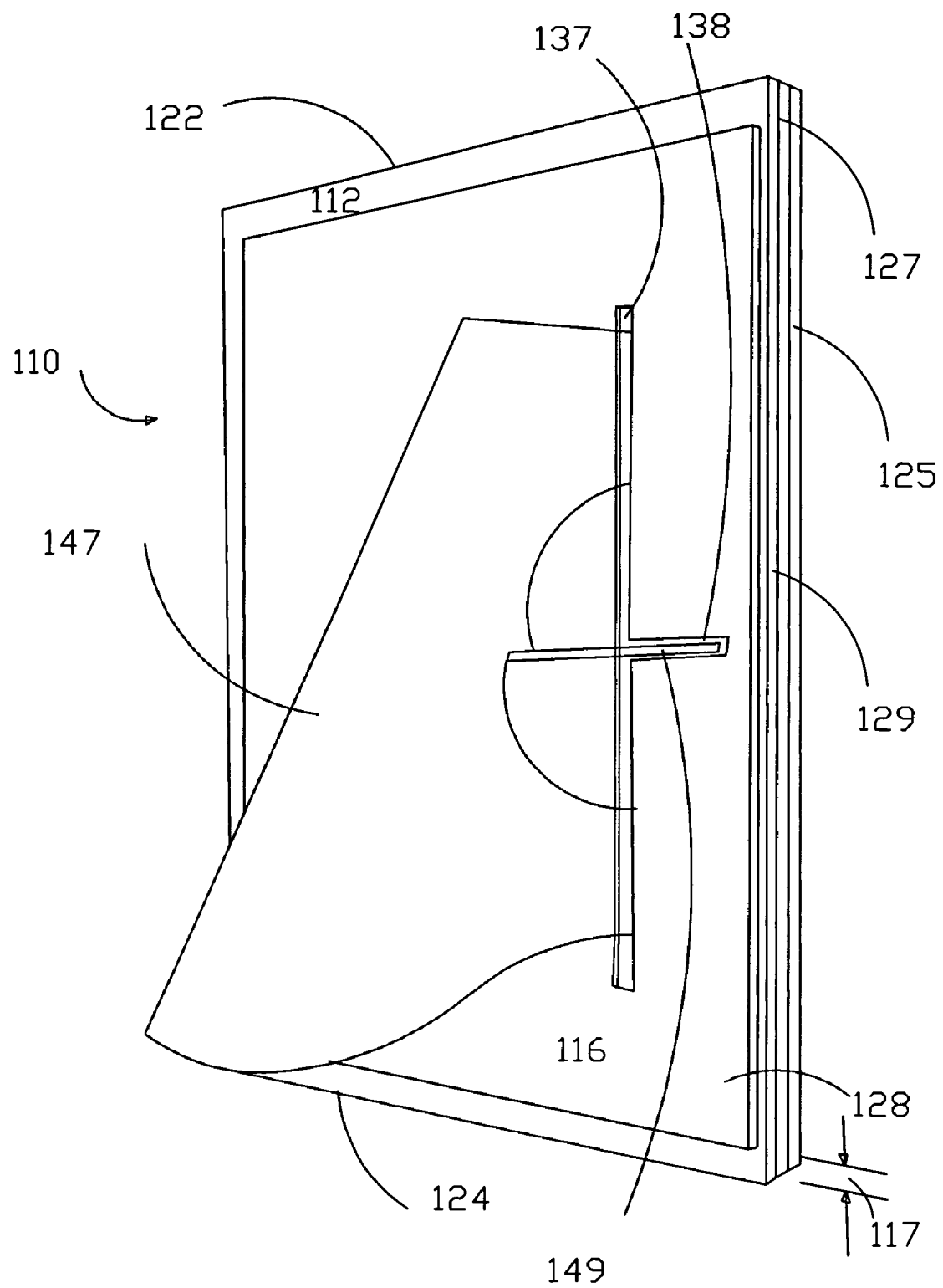
FIG. 7 is a rear perspective view of a second embodiment of the present invention having the scent board mounted thereon and a second scent board partially engaging the foot.

Referring to FIG. 7, a rear perspective of the scented picture frame shows the foot 147 engaged to the lock 149. The scent board 128 has vertical slot 137 adapted to receive foot 147. Scent board 128 further comprises horizontal slot 138 adapted to receive lock 149. Scent board 128 is sized to be smaller than the body 112 to minimize visibility of the scent board from a viewing position adjacent the front sheet 125. The spacer layer 127 holds the front sheet in spaced relation to the support 129 on the back 116. The scent sheet 128 is sized to provide a stand off 117 between the scent board bottom 132 and the table or support under the standing scented picture frame to protect against the scent on the scent board leaching onto the table. The standoff 117 is a space between the bottom of the body 124 and the bottom 132 of the scent board 128.

In use, the picture frame 10 is shipped with one or more scent boards 28, 128 for removably attaching to the frame 10 to form a scented picture frame 10. The picture frame is preferably made of a fiber material such as paper, cardboard, fiber board, or other lightweight easy to cut material, however the components of the body 12, 112 may alternatively be made from plastic, ceramic, glass or metal. The scent boards 28, 128 are made of a porous or absorbable material such as paper or cardboard. Either or both of the frame body 12 or the scent board 28 may be made of an absorbent plastic material such as foam or the like. The sheet holder on the back comprising a tab 50 or foot 147 may be a separate device attached to the back by glue or staple or the like and folded out from the back for engaging the slot in the scent board. Alternatively, the sheet holder may be integrally formed in the back of the body by die cutting the shape in the support layer and folding the holder outward from the body to support the scent board.

The scent boards 28, 28a, 128, 128a may be impregnated with a variety of scents and aromatherapy solutions. The scent boards are individually sealed for holding in the scent until use. The scent board may be scented on only one side to prevent mixing scents when used in combination with a different scented scent board. The scent board is usually impregnated with a scent carried in an oil or other liquid for application. The scent board may be impregnated with scents selected from oil and aroma ingredients to simulate a smell selected from the list of: a variety of perfumes, food and flower smells, new car or evergreen or other commercial fragrances, berries, animals and smoke scents. Alternatively, the scent board may be impregnated with aromatherapy mixtures such as Lavendar, Ylang Ylang, Mandarin, Sandalwood, Vetiver, Patchouli, Lemon, and Peppermint and the like or combinations thereof.

Although the invention has been described above in connection with particular embodiments and examples, it will be appreciated by those skilled in the art that the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

I claim:

1. A scented picture frame comprising:
 a frame having a body comprising a front, a back, a first side, a second side, a top and a bottom;
 a face sheet on the front of the frame, a picture window formed in the face sheet;
 a spacer sheet adjacent the face sheet and intermediate the front and the back, the spacer sheet having a picture cavity adjacent the picture window, a picture pouch in the picture cavity;
 a first scent board having a front, a back and a slot, the slot extending from the front to the back, the first scent board removably attached to the back of the frame; and
 a tab on the back of the frame, the tab having a base and a tip, the base on the back of the frame, the tip spaced from the back of the frame, the slot configured to matingly accept the tab, the tab in the slot wherein the first scent board is hanging on the tab intermediate the tip and the base of the tab, the first scent board adjacent the back of the frame.

2. The invention of claim 1 wherein the first scent board further comprises a plurality of slots for removably connecting the scent board to the frame.

3. The invention of claim 1 further comprising a prop on the frame adapted to hold the frame in a viewable position.

4. The invention of claim 1 wherein the frame further comprises a support sheet on the back, the tab integrally formed in the support sheet, the tip die-cut in the support sheet, wherein the tab is folded away from the body to receive the first scent board.

5. The invention of claim 1 further comprising a second scent board removably on the frame, the second scent board adjacent the first scent board.

6. The invention of claim 1 wherein the frame further comprises a foot extending from the back, the first scent board on the foot 7. The invention of clam 6 further comprising a lock on the frame, the lock engaged with the foot, the first scent board further comprising a second slot, the foot in the second slot, the lock in the first slot.

8. The invention of claim 7 further comprising a second scent board on the frame, the second scent board having a vertical slot and a horizontal slot, the vertical slot and the horizontal slot adapted to engage the foot and lock whereby the second scent board is removably on the frame adjacent the first scent board.

9. The invention of claim 1 further comprising a second scent board, the second scent board comprising a slot, the tab in the second scent board slot to removably hold the second scent board on the frame, the second scent board adjacent the first scent board.

10. The invention of claim 9 further comprising a knob on the first scent board the knob bearing against the second scent board, a space intermediate the first scent board and the second scent board.

11. A scented picture frame comprising:
 a body, the body comprising a front and a back, the back further comprising a support sheet;
 a first scent board, the first scent board having a front and a back and a slot, the slot extending from the front of the scent board to the back of the scent board and forming an opening, the front of the first scent board adjacent the back of the body, a scent impregnated in the first scent board;

a sheet holder on the support sheet extending from the back of the body, the sheet holder removably in the slot of the scent board wherein the scent board is removably attached to the body by the sheet holder extending into the slot, the first scent board adjacent to the back of the body.

12. The invention of claim 11 wherein the sheet holder comprises a tab, the tab having a base and a tip, the base on the back of the body, the tip spaced from the back, the slot configured to matingly accept the tab, the tab in the slot wherein the first scent board is hanging on the tab intermediate the tip and the base, the first scent board adjacent the back of the body.

13. The invention of claim 12 further comprising a second scent board on the tab, the second scent board having a front, a back and a slot extending therethrough, the tab in the slot.

14. The invention of claim 12 further comprising a second scent board on the tab wherein the first scent board further comprises a first scent and the second scent board further comprises a second scent.

15. The invention of claim 11 wherein the sheet holder further comprises a foot extending from the support sheet, the foot matingly extending into the slot of the first scent board, the foot holding the first scent board adjacent the back of the body.

16. The invention of claim 15 wherein the sheet holder further comprises a lock, the lock engaging the foot, the first scent board further comprising a horizontal slot, the horizontal slot adapted to matingly receive the lock wherein the scent board is held adjacent the back of the body.

17. The invention of claim 16 further comprising a second scent board on the sheet holder, the second scent board having a front, a back and a plurality of slots extending therethrough, the foot in one of the plurality of slots, the lock in another of the plurality of slots.

18. A scented picture frame comprising:

a body having a front, a back, a top and a bottom, a picture window on the front, a prop on the body;

a sheet holder on the back of the body, the sheet holder extending from the back;

a first scent board removably hanging on the sheet holder adjacent the back, the first scent board having a front, a back, and a slot extending from the front of the scent board to the back of the scent board having the sheet holder removably therein.

19. The invention of claim 18 wherein the sheet holder further comprises a tab comprising a tip, and a base, the base on the back of the body, the tab holding the tip spaced from the back of the body, the tab in the slot wherein the first scent board is hanging on the tab intermediate the tip and the base.

* * * * *